United States Patent [19]

Okada et al.

[11] Patent Number: 5,082,770

[45] Date of Patent: Jan. 21, 1992

[54] METHOD FOR QUANTITATIVE DETERMINATION OF POLYAMINES

[75] Inventors: Masato Okada, Yokohama; Makoto Sakamoto, Fujisawa, both of Japan

[73] Assignee: Tokuyama Soda Co., Ltd., Tokuyama, Japan

[21] Appl. No.: 176,885

[22] Filed: Apr. 4, 1988

[30] Foreign Application Priority Data

Apr. 4, 1987 [JP] Japan .................................. 62-82206
Apr. 20, 1987 [JP] Japan .................................. 62-95218

[51] Int. Cl.$^5$ .......................... C12Q 1/32; C12Q 1/26; C12N 9/04
[52] U.S. Cl. ........................................ 435/26; 435/25; 435/18; 435/19; 435/189; 435/190; 435/183; 435/859
[58] Field of Search .................... 435/25, 26, 18, 19, 435/189, 190, 183, 803, 814, 815, 859

[56] References Cited

U.S. PATENT DOCUMENTS

| | | | |
|---|---|---|---|
| 3,929,580 | 12/1975 | Forgione et al. | 195/99 |
| 4,444,880 | 4/1984 | Tom | 435/7 |
| 4,460,684 | 7/1984 | Bauer | 435/14 |
| 4,550,078 | 10/1985 | Yamada et al. | 435/25 |

FOREIGN PATENT DOCUMENTS 184919A 10/1986 European Pat. Off. .
274698A 8/1986 Japan .

OTHER PUBLICATIONS

Rosemblatt, M. S. et al., *Biochemistry*, vol. 13, No. 20, pp. 4176-4180 (1974).
Bachrach and Plesser, *Anal. Biochem.*, 152, 423-431 (1986).
Russel & Russel, *Clin. Chem.*, 21, No. 7, 860-863 (1975).

*Primary Examiner*—Esther L. Kepplinger
*Assistant Examiner*—Toni R. Scheiner
*Attorney, Agent, or Firm*—Morgan & Finnegan

[57] ABSTRACT

A method for the quantitative determination of polyamines, which comprises allowing a polyamine oxidizing enzyme, an ω-aminoalkylaldehyde dehydrogenase, an oxidized nicotinamide coenzyme and, as required, an acylpolyamine anidohydrolase to act upon a sample solution containing polyamines (for example, urine, blood and other kinds of body fluid), and measuring the reduced nicotinamide coenzyme thus formed by, for example, colorimetry, thereby determining the amount of said polyamines.

27 Claims, No Drawings

METHOD FOR QUANTITATIVE DETERMINATION OF POLYAMINES

BACKGROUND OF THE INVENTION

1. Field of the Invention

This invention relates to a new method for the quantitative determination of polyamines. More particularly, it relates to a method which can accurately determine the amount of polyamines by a simple process.

2. Description of the Prior Art

Polyamines, widely distributed in living bodies, are substances of medical importance because these are found in large quantities in proliferating cells, especially in tumor cells. Russell, et.al. reported in 1975 that the body fluids (e.g., urine and blood) of cancer patients, as compared with normal persons, contain a larger amount of polyamines. Since then, many researchers have studied the correlation between cancer and the content of polyamines in body fluids, and confirmed the validity of the report by Russell, et.al. Quantitative determination of polyamines in body fluids is very difficult because of the extremely low concentration of polyamines and the presence of many other substances in the test sample. Recently, an enzymatic method has received attention as a means to rapidly determine the amount of polyamines in body fluids. In a typical example, a sample solution containing polyamines is allowed to react with an enzyme capable of oxidizing polyamines (hereinafter referred to as polyamine oxidizing enzyme) to form hydrogen peroxide, which is then introduced to a color-developing system comprising 4-aminoantipyrine, phenol and a peroxidase, followed by colorimetric measurement of the dye formed.

The problem involved in this method is that the hydrogen peroxide formed tends to undergo decomposition by reducing agents present in body fluids, such as ascorbic acid and uric acid. Hence, these reducing agents must be previously removed or separated from the sample solution to obtain an accurate determination of polyamines, thus complicating the operations involved and increasing the time required for analysis. In addition, this method, based on the measurement of hydrogen peroxide, has an inherent problem resulting in measurement errors due to the unavoidable lost of this unstable compound.

SUMMARY OF THE INVENTION

An object of this invention is to provide a new method for accurately determining the amount of polyamines.

A further object of this invention is to provide a new method for determining the amount of polyamines by a simple process.

Another object of this invention is to provide a simple method for accurately determining the amount of polyamines contained in body fluid.

Other objects of this invention will become apparent from the descriptions given below.

This invention relates to a method for the quantitative determination of polyamines, which comprises: allowing a polyamine oxidizing enzyme, an ω-aminonalkylaldehyde dehydrogense and an oxidized nicotinamide coenzyme to act upon a sample solution containing polyamines, and measuring the reduced nicotinamide coenzyme thus formed to determine the amount of the polyamines.

Unlike the conventional method which involves, as a major step, measurement of hydrogen peroxide formed from the reaction of polyamine oxidizing enzyme on a polyamine, the principal feature of this invention involves, as a major step, measurement of an aminoaldehyde which is formed together with hydrogen peroxide.

The reaction mechanism of the method of this invention is not completely clear yet, but may be presumed as described below. A polyamine contained in a sample solution is converted to ω-aminoalkylaldehyde by the action of a polyamine oxidizing agent, which in turn is allowed to react with an oxidized nicotinamide coenzyme by the action of ω-aminoalkylaldehyde dehydrogenase, and the amount of the reduced form of the nicotinamide coenzyme formed by this reaction is assayed. The amount of polyamine can be obtained from the quantitative relationship between polyamine and the reduced-form of nicotinamide coenzyme previously determined using samples of known polyamine concentrations.

The method of this invention can be applied to any type of samples containing polyamines, but is most effective when applied to body fluids, such as urine, blood and bile.

PREFERRED EMBODIMENTS OF THE INVENTION

Polyamines that can be measured by the method of this invention are free polyamines (hereinafter referred to simply as polyamines), such as spermidine, putrescine, spermine and cadaverine. When measuring conjugated polyamines present in the urine (acetyl derivatives of these free amines), the method of this invention can be applied after the acetylpolyamines have been hydrolyzed by the known technique of using an acyl-polyamine amidohydrolase. This hydrolysis should preferably be carried out prior to, or simultaneously with the conversion of polyamines to ω-aminoalkylaldehydes.

The first step of the method of this invention is the conversion of polyamines to ω-aminoalkylaldehydes by the action of a polyamine oxidizing enzyme. The aldehydes thus formed have a higher stability against the reducing substances contained in sample solutions compared with hydrogen peroxide, and hence can be used for the precise determination of polyamines even in the presence of reducing substances. Any known enzymes capable of oxidizing polyamines to form equimolar amounts of ω-aminoalkylaldehydes may be used for the purpose of this invention. Typical examples include putrescine oxidases of microbial origin derived from strains of the genera Micrococcus, Nocardia, Aspergillus Pseudomonas and Arthrobacter; putrescine oxidase of plant origan derived from germinated soybean and the like; and putrescine oxidases of animal origin derived from pig kidney and the like.

When a polyamine oxidizing enzyme that will not act upon spermine, for example putrescine oxidase, is used, it is necessary to previously convert the spermine in the sample solution to putrescine and to remove 3-aminopropanal thus formed by column treatment or other suitable methods. Any known technique may be employed for the conversion of spermine to putrescine, but the use of an enzyme having such an activity is preferable. Typical examples of such enzymes include polyamine oxidase of animal origin derived from bovine plasma, rat liver and the like, and those of microbial origin derived from strains of genera Aspergillus, Penicillium and Streptomyces.

It is also possible to convert spermine directly to the corresponding ω-aminoalkylaldehyde, N-(3-aminopropyl)aminobutyl aldehyde, by using an enzyme having such an activity, thus eliminating the need for column treatment and other intricate operations. As examples of such enzymes may be mentioned polyamine oxidases of plant origin derived from barley, oats, corn and peas.

It is known that polyamines in the urine are mainly conjugated spermidine, putrescine and cadaverine (acetyl derivatives of these free polyamines). Hence, when analyzing a urine sample, use of putrescine oxidase alone will serve the purpose. In this case, the method of this invention may be applied simultaneously with or after hydrolysis of the acetylpolyamines by the known technique of using an acylpolyamine amidohydrolase.

Acylpolyamine amidohydrolases are enzymes capable of cleaving the amide linkage in an acylpolyamine to form free polyamine. These can be obtained from animal organs, such as the liver, kidney, pancreas and heart of cattle, pigs and chickens, or may be produced by a variety of microorganisms. In the latter case, strains of Streptomyces, particularly Streptomyces avellaneus R-20 (FERM-P No. 5443), are preferably used.

Any well-known conditions may be adopted for the action of polyamine oxidizing enzyme, and, as required, for the enzyme action to convert spermine to putrescine and/or for the enzyme action to convert it to N-(3-aminopropyl)aminobutyl aldehyde, upon the polyamine containing sample solutions. Generally, the reaction is preferably carried out near or at the optimum pH and optimum temperature of the enzyme used. The suitable amount of enzyme to be used varies with its activity and reaction conditions, but is generally in the range from 0.01 to 50 units, preferably form 0.1 to 30 units.

Any type of ω-aminoalkylaldehyde dehydrogenase capable of reacting with a ω-aminoalkylaldehyde to form an equimolar amount of the reduced-form of nicotinamide coenzyme in the presence of oxidized nicotinamide coenzyme may be used for the purpose of this invention. The most preferred ω-aminoalkylaldehyde dehydrogenase to be used in the method of this invention is 4-aminobutanal dehydrogenase having the following properties.

(1) Action
   Acts upon 4-aminobutanal in the presence of oxidized nicotinaminde adenine dinucleotide or oxidized nicotinamide adenine dinucleotide phosphate to form 4-aminobutyric acid and reduced nicotinamide adenine dinucleotide or reduced nicotinamide adenine dinucleotide phosphate.
(2) Substrate specificity
   Coacts with oxidized nicotinamide adenine dinucleotide and oxidized nicotinamide adenine dinucleotide phosphate as oxidized nicotinamide coenzyme, and upon 4-aminobutanal and
(3) Optimum pH: 7.7 - 8.3
(4) pH Stability
   More than 90% activity is retained at a pH in the range from 4.5 to 8.5 when stored at 5° C. for 24 hours.
(5) Molecular weight: 102,000+5,000
(6) Molecular weight of subunits: 50,000+5,000
(7) Number of subunits: 2

The 4-aminobutanal dehydrogenase can be obtained by growing a strain of Micrococcus capable of producing the same. Any type of medium may be used for this purpose so long as it contains carbon sources (e.g., glucose), nitrogen sources (e.g., polypeptone) and inorganic salts. The enzyme productivity can be enhanced if a polyamine, such as putrescine, spermidine, diaminopropane and cardine, is further added to the culture medium. Cultivation is preferably carried out at a temperature in the range from 15° C. to 40° C., most preferably, from 20° C. to 35° C., and at a pH in the range from 4.0 to 9.0, most preferably from 5.0 to 8.0. There is no specific limitation on the culture time, but the time after the start of the resting period should preferably be within ten hours in terms of enzyme productivity and economic factors.

The grown microbial cells can be isolated from the culture solution by centrifugal separation, filtration and other known methods, centrifugation is the most preferred.

4-Aminobutanal dehydrogenase usually accumulates inside the microbial cells and can be extracted by methods commonly used for enzyme extraction, such as cell breakdown by milling or ultrasonic treatment, and destruction of cell walls by the action of an enzyme (e.g., lysozyme) or destruction of cell membrane with an organic solvent (e.g., toluene).

The solution of crude enzyme thus obtained may be further purified, as required, by suitably combining or repeating techniques commonly used for enzyme purification: such as, precipitation with ammonium sulfate, ion-exchange chromatography, gel filtration, hydroxyapatite column chromatography and preparative electrophoresis The activity of 4-aminobutanal dehydrogenase is measured and expressed as described below.

0.1M tris(hydroxymethyl)aminomethane-HCl buffer solution (pH: 8.0; 2.5 ml) containing 10mM putrescine dihydrochloride is placed in a cuvette (optical width: 1 cm), 20 ul (5 units) of putrescine oxidase derived from a strain of Micrococcus is added, and the mixture is incubated at 30° C. for ten minutes. To the resulting solution, are added 0.5 ml of 20mM aqueous solution of NAD and 50 ul of sample solution containing 4-aminobutanal dehydrogenase in that order, and the rate of increase in absorbance at 340 nm is measured. The enzyme activity for 1.0 ml sample solution can be calculated from the increase in absorbance per minute (A) using the following conversion equation (1), in which the amount of enzyme that forms 1 umole NADH is taken as 1 unit (umole/min).

$$\text{Enzyme Activity Value} = \frac{A}{6.2} \times \frac{3.07}{0.05} \quad (1)$$

The relative activity of 4-aminobutanal dehydrogenase used in this invention is 120 to 140 units/mg protein. Electrophoresis of this enzyme on polyacrylamide gel shows a single protein band both in the presence and in the absence of sodium dodecyl sulfate.

The aforementioned ω-aminoalkylaldehyde dehydrogenases may be subjected to reaction under any conditions that allow the action of these enzymes. Generally, however, the reaction should preferably be carried out near or at the optimum pH and optimum temperature of the enzymes used. The enzyme concentration is usually in the range from 0.1 to 50 units.

Any known type of oxidize nicotinamide coenzyme may be used in the method of this invention, illustrative examples being oxidized nicotinamide adenine dinucleotide (NAD) and oxidized nicotinamide adenine dinucleotide phosphate (NADP). These coenzymes act as hydrogen acceptors in the reaction, forming reduced nicotinamide adenine dinucleotide (NADH) and reduced nicotinamide adenine dinucleotide phosphate (NADPH), respectively.

In the method of this invention, all of the enzymes (polyamine oxidizing enzyme, ω-aminoalkylaldehyde dehydrogenase, oxidized nicotinamide coenzyme and, as required, acylpolamine amidohydrolase) are usually allowed to act upon the sample solution simultaneously. However, a two-step technique, addition of polyamine oxidizing coenzyme and ω-aminoalkylaldehyde dehydrogenase, may also be adopted. This is because a polyamine in the sample solution is first converted to the corresponding ω-aminoalkylaldehyde by the action of polyamine oxidizing enzyme, which in turn reacts with oxidized nicotinamide coenzyme by the action of ω-aminoalkylaldehyde dehydrogenase, thus forming the reduced-form of nicotinamide coenzyme.

The reaction of this invention may be carried out under any conditions that allow each of the enzymes used to act normally. The preferable pH is generally in the range from 6.5 to 8.5. Simultaneous action of the enzymes may be effected in several ways: simultaneous addition of all the enzymes to the sample solution; addition of ω-aminoalkylaldehyde dehydrogenase while the oxidation of polyamines by polyamine oxidizing enzyme is in progress; and addition of ω-aminoalkylaldehyde dehydrogenase, followed by addition of polyamine oxidizing enzyme.

In the method of this invention, any known technique for the quantitative determination of reduced nicotinamide coenzyme may be used. The most preferred one is a colorimetric method, in which reduced nicotinamide coenzyme is converted to a formazan dye by the action of a color-developing system composed of a tetrazolium salt and an electron carrier. Any type of tetrazolium salt, including mono- and di-tetrazolium salts, may be used for the purpose of this invention. Illustrative examples include: 3-(p-iodophenyl)-2-(p-nitrophenyl)-5-phenyl-2H-tetrazolium chloride (hereinafter abbreviated as INT); 3,3'-(3,3'-dimethoxy-4,4'-biphenylene)-bis [2-(p-nitrophenyl)-5-phenyl-2H-tetrazolium chloride (hereinafter Nitro-TB); 3,3'-(4,4'-biphenylene)-bis(2,5-diphenyl-2H-tetrazolium chloride) (hereinafter Neo-TB), 3,3'-(3,3'-dimethoxy-4,4'-biphenylene)-bis[2,5-bis(p-nitrophenyl)-2H-tetrazolium chloride) (hereinafter TNTB); and 3,3'-(3,3'-dimethoxy-4,4'-biphenylene)-bis[2,5-diphenyl-2H-tetrazolium chloride) (hereinafter TB). Of these, INT (monotetrazolium salt) and Nitro-TB (ditetrazolium salt) are the most preferred. Suitable concentration of the tetrazolium salt may vary with the other reaction conditions, but is generally in the range from 0.1 to 50 mM. The electron carrier serves to transport hydrogen from the reduced-form of nicotinamide coenzyme to the tetrazolium salt, thus converting it to a formazan dye having a resonating structure. Illustrative examples include diaphorase and 1-methoxy-5methylphenazinium methyl-sulfate (hereinafter 1-methoxy-PMS), of which the use of diaphorase is preferred. The suitable amount used may vary with the reaction conditions, but is usually in the range from 0.1 to 50 units.

The amount of reduced nicotinamide coenzyme is most preferably determined by allowing a tetrazolium salt to act upon a sample solution containing said coenzyme at a pH level in the range from 4 to 7 (preferably from 5 to 6.5) in the presence of a nonionic surfactant in an amount of 0.3 to 10 weight %, preferably 0.5 to 2 weight %, measuring the intensity of color thus developed by a known colorimetric method, and calculating the amount of coenzyme from the quantitative relationship between polyamine and reduced-form of nicotinamide coenzyme previously determined using samples of known polyamine concentrations.

The pH of sample solution may be adjusted by any known methods, preferably by the use of a buffer solution (pH control region: 4 to 7). For example, buffers of amino acid type and some Good's buffers, such as MES [2-(N-morpholino)ethanesulfonic acid monohydrate], Bis-Tris [bis(2-hydroxyethyl-imino-tris(hydroxymethyl)methane] and PIPES [piperazine-N,N,-bis(2ethanesulfonic acid)] buffers, are preferably used. The pH should be controlled at a level in the range form 4 to 7, most preferably in the range from 5 to 6.5 when consideration is given to the stability of the electron carrier (e.g., diaphorase). The buffer solution may be used at any concentrations that ensure stable pH control, usually at level in the range from 0.1 to 1.0M.

There is no specific limitation upon the type of nonionic surfactant used in the method of this invention so long as it does not retard the reaction. However, polyoxyethylene alkylaryl ethers, polyoxyethylene-styrenated-phenols, polyoxyethylene alkyl ethers, polyoxyethylene higher-alcohol ethers and polyoxyethylene fatty acid esters are preferably employed in terms of the stability and molecular extinction coefficient of the formed formazan dye and the precipitation preventing effect. Illustrative examples include Emulgen 935 ®, Penerol N-100N/C ®, Penerol SP-24 ®, Emulsit 25 ® and Triton X-100 ®. These surfactants exhibit their effect at a concentration in the range from 0.3 to 10 weight % as mentioned above, but the reaction is preferably carried out in the presence of a nonionic surfactant in an amount of 0.5 to 2.0 weight %.

The method for the quantitative determination of reduced nicotinamide coenzyme described above has the advantage in that the use of a large amount of nonionic surfactant makes it possible to effect colorimetric measurement on the acidic side. In the conventional methods, a color developer is added to a mixture in which reduced nicotinamide coenzyme has been formed under an acidic condition, and the color is developed and measured under an alkaline condition. Such development and measurement of color under an alkaline condition is often adversely affected by reducing substances contained in body fluids, which makes it difficult to correctly determine the amount of the coenzyme. Thus, the method of this invention which allows colorimetric measurement under an acidic condition provides a very important technique that surmounts the above-mentioned problem associated with conventional methods. Another advantage is that the nonionic surfactant and color developer need not necessarily be added to the system in which reduced nicotinamide coenzyme has been formed, but these may be added to the sample solution containing polyamines simultaneously with, or prior to, the addition of the above-mentioned enzymes.

Colorimetric measurement may be carried out under an acidic condition, for example, at a pH below 4, set independently of the pH range of 4 to 7 required for color development.

In the method for the quantitative determination of reduced nicotinamide coenzyme detailed above, the tetrazolium salt can be used at concentrations over a wide range because it does not undergo reduction with reducing substances contained in the sample solution, e.g., body fluid. Hence, this method is applicable not only to the determination of reduced nicotinamide coenzyme derived from polyamines, but also to many other cases, for example, for the determination of reduced nicotinamide coenzyme formed by the reaction routes listed below.

1. Lactate dehydrogenase
   L-lactate + $NAD^+$ ⇌ Pyruvate + NADH + $H^+$
2. Isocitrate dehydrogenase
   Isocitrate + $NAD(P)^+$ ⇌ 2-Oxoglutarate + $CO_2$ + NAD(P)H
3. Gluclose-6-phosphate dehydrogenase
   D-Blucose-6-phosphate + $NADP^+$ ⇌ D-glucono-δ-actone-6-phosphate + NADPH + $H^+$
4. Galactose dehydrogenase
   D-Galactonfuranose + $NAD^+$ ⇌ D-Galactone-δ-lactone + NADH + $H^+$
5. Pyruvate dehydrogenase
   Pyruvate + CoA-SH + $NAD^+$ ⇌ Acetyle-S-CoA + $CO_2$ + NADH + $H^+$
6. Alcohol dehydrogenase
   $R$-$CH_2OH$ + $NAD(P)^+$ ⇌ R-CHO + NAD(P)H + $H^+$
7. Glycerol dehydrogenase
   Glycerol + $NAD^+$ ⇌ Dihydroxyacetone + NADH + $H^+$
8. D-Xylulose reductase
   Xylitol + $NAD^+$ ⇌ D-Xylulose + NADH + $H^+$
9. Malate dehydrogenase
   L-Malate + $NAD^+$ ⇌ Oxaloacetate + NADH
10. Glucose dehydrogenase β-D-Glycopyranose + $NAD(P)^+$ ⇌ D-Glucono-δ-lactone + NAD(P)H + $H^+$
11. 6-Phosphogluconate dehydrogenase
    6-Phospho-D-gluconate + $NAD(P)^+$ ⇌ 2-keto-6-phospho-D-gluconate + NAD(P)H
12. Ureidoglycollate dehydrogenase
    Ureidogylcollate + $NAD(P)^+$ ⇌ Oxalurate + NAD(P)H + $H^+$
3. Formate dehydrogenase
   Formate + $NAD^+$ ⇌ $CO_2$ + NADH
14. Aldehyde dehydrogenase
    R-CHO + $NAD^+$ + $H_2O$ ⇌ $R$-$COO^-$ + NADH + $2H^+$
15. Alanine dehydrogenase
    L-Alanine + $H_2O$ + $NAD^+$ ⇌ Pyruvate + $NH^{30}_4$ + NADH + $H^+$
16. Glutamate dehydrogenase
    L-Glutamate + $H_2O$ + $NAD^+$ ⇌ 2-Oxoglutarate + $NH^+_4$ + NADH + $H^+$
17. Serine dehydrogenase
    Serine + $NAD^+$ + $H_2O$ ⇌ Hydroxypyruvate + NADH + $NH^+_4H^+$
18. Valine dehydrogenase
    Valine + $H_2O$ + $NADP^+$ ⇌ 2-Oxoisovalerate + $NH^+_4$ + NADPH + $H^+$
9. Leucine dehydrogenase
   L-Leucine + $H_2O$ + $NAD^+$ ⇌ 2-Oxoisocaproate + $NH^+_4$ + NADH + $H^+$
20. Glycine dehydrogenase
    Gylcine + $H_2O$ + $NAD^+$ ⇌ Glyoxylate + $NH^+_4$ + NADH + $H^+$
21. 3α-Hydroxoysteroid dehydrogenase
    3α-Hydroxysteroid + $NAD(P)^+$ ⇌ 3-Oxosteroid + NAD(P)H + $H^+$ The following examples will further illustrate the invention but are not intended to limit its scope.

Reference Example

A 240 umole/l solution of acetylpolyamines (acetylputrescine:acetylcadaverine:acetylspermidine = 8:1:1, the acetylspermidine being composed of N1-acetylspermidine : N8-acetylspermidine = 3:1) was made, and serial dilutions thereof were prepared. Each of the dilutions, 0.5 ml, was mixed with 0.5 ml of Reagent 1 shown in Table 1, and the mixture was heated at 37° C. for 20 minutes. 0.5 ml of Reagent 2, shown in Table 2, was then added, and the reaction was continued at 37° C. for five minutes at pH 6.0 and at a surfactant concentration of 1.33 weight %. After addition of 0.5 ml of 1 M hydrochloric acid, the absorbance at 530 nm was measured. The absorbance data for the various polyamine concentrations are summarized in Table 3.

Separately, a 200 umole/l solution of polyamines (putrescine:cadaverine:spermidine = 3:1:1) was made, and serial dilutions thereof were prepared. Each of the dilutions, 0.5 ml, was mixed with 0.5 ml of a reagent having a composition U similar to that of Reagent 1 except that the acylpolyamine amidoydrolase was eliminated, and the mixture was heated at 37° C. for 20 minutes. 0.5 ml of Reagent 2 was then added, and the raection was continued at 37° C. for five minutes at pH 6.0 and at a surfactant concentration of 1.33 weight %. After addition of 0.5 ml of 1M hydrochloric acid, the absorbance at 530 nm was measured. The data thus obtained are also shown in Table 3.

TABLE 1

| (Reagent 1) | |
|---|---|
| Acylpolamine amidohydrolase (derived from *Streptomyces*) | 240 u* |
| Putrescine oxidase (derived from *Micrococcus*) | 80 u |
| ω-Aminoalkylaldehyde dehydrogenase (derived from *Micrococcus*) | 10 u |
| Oxidized nicotinamide coenzyme (Wako Junyaku Co., Ltd.) | 10.2 mg |
| Ascorbate oxidase (Toyo Jozo Co., Ltd.) | 45 u |
| Emulgen 935 | 0.4 g |
| Oxamic Acid (Aldrich Chemical Company, Inc.) | 45.6 mg |

*u = Units
The above components are dissolved in 10 ml of 0.4M Tris-HCl buffer, pH 8.0.

TABLE 2

| (Reagent 2) | |
|---|---|
| Nitro Tetrazolium Blue (Dojin Chemical Research Laboratories) | 5.0 mg |
| Diaphorase (Oriental Enzyme Co., Ltd.) | 80 u |

The above components were dissolved in 20 ml of 0.6M MES buffer, pH 6.0 (Dogin Chemical Research Laboratories).

TABLE 3

| Polyamine concn. (uM) | Absorbance | |
|---|---|---|
| | Conjugated polyamine | Free polyamine |
| 0 | 0 | 0 |
| 40 | 0.182 | 0.180 |
| 80 | 0.363 | 0.362 |
| 120 | 0.545 | 0.535 |
| 160 | 0.727 | 0.721 |
| 200 | 0.908 | 0.910 |

TABLE 3-continued

| Polyamine concn. (uM) | Absorbance | |
|---|---|---|
| | Conjugated polyamine | Free polyamine |
| 240 | 1.090 | — |

The data of Table 3 show a linear relationship between polyamine concentration and absorbance, indicating that both conjugated and free polyamines can be colorimetrically measured.

The ω-aminoalkylaldehyde dehydrogenase used in Table 1 was prepared according to the procedure described below. Micrococcus flavidus was inoculated to 10 liters of a medium, at pH 7.5, containing 0.5% glucose, 0.5% peptone, 0.1% NaCl, 0.2% yeast extract and 0.04% of a surface-active agent (LG294; Asahi Denka Kogyo K.K.), and incubated at 26° C. for 24 hours. The master culture thus obtained was added to 160 liters of a medium at pH 6.5, containing 0.5% glucose, 0.5% peptone, 0.13% NaCl, 0.15% yeast extract, 0.3% putrescine and 0.04% LG294, and cultivation was continued at 26° C. for 24 hours. The grown microbial cells, 3 Kg, were collected by centrifugation, washed with 0.01M phosphate buffer at pH 7.0, suspended in the same type of phosphate buffer, and disrupted in a mill. The suspension of cell debrise thus obtained was centrifuged and the supernatant was collected, giving a solution of crude ω-aminoalkylaldehyde dehydrogenase (about 80,000 units).

This solution was passed through a 5.0 liters DE-52 column, previously equilibrated with 0.01M phosphate buffer, pH 7.0. The column was washed with the same type of phosphate buffer containing 0.1M ammonium sulfate, and the absorbed ω-aminoalkylaldehyde dehydrogenase was eluted with the same type of phosphate buffer containing 0.4M ammonium sulfate.

The elute thus obtained was subjected to repeated desalting with 0.01M phosphate buffer of pH 7.0, and concentrated to afford a solution of ω-aminoalkylaldehyde dehydrogenase, 40,000 units. The recovery rate was 50% based on the solution of crude product.

EXAMPLE 1

Quantitive Determination Of Polyamines In Blood

To 1.0 ml of a blood sample was added 1.0 ml of 10% trichloroacetic acid solution, and the mixture was vigorously stirred to effect protein removal and centrifuged at 3,000 rpm for five minutes. 1.0 ml of the supernatant was collected and neutralized by addition of 1.0 ml of 0.3M solution of tris(hydroxymethyl) aminomethane giving a test solution.

To 0.5 ml of this test solution was added 0.5 ml of a reagent, Reagent 1,' having a composition similar to that of Reagent 1 except that 240 units of the acylopolyamine amidohydrolase derived from Streptomyces, was replaced by 50 units of polyamine oxidase derived from barley, and the mixture was heated at 37° C. for 20 minutes at pH 8.0. 0.5 ml of Reagent 2 was then added, and reaction was continued at 37° C. for five minutes at pH 6.0 and at a surfactant concentration of 1.33 weight %. After addition of 0.5 ml of 1M hydrochloric acid, the absorbance at 530 nm ($E_s$) was measured. Separately, 0.5 ml of Reagent 3 shown in Table 4 was added to 0.5 ml of the test solution, and the mixture was heated at 37° C. for 20 minutes, and then treated in the same manner as above to measure the absorbance of the blank ($E_s'$).

TABLE 4

| (Reagent 3) | |
|---|---|
| Oxidized nicotinamide coenzyme (Wako Junyaku Co., Ltd.) | 10.2 mg |
| Ascorbate oxidase (Toyo Jozo Co., Ltd.) | 45 u |
| Emulgen 935 (Kao Soap Co., Ltd.) | 0.4 g |
| Oxamic Acid (Aldrich Chemical Company, Inc.) | 45.6 mg |

The above components are dissolved in 10 ml of 0.4M Tris-HCl buffer, pH 7.8.

On the other hand, absorbance was also measured for 30 uM solution of putrescine dihydrochloride (as standard) and for pure water (as test blank) according to the methods used for measurement of $E_s$ and $E_s'$, $E_{st}$ and $E_{st}'$ for the standard, and $E_{H_2O}$ and $E_{H_2O}'$ for the test blank. The measuring methods described above are summarized in Table 5.

The amount of polyamines in the blood sample can be calculated from the absorbance data obtained above using the following equation:

TABLE 4

| (Reagent 3) | |
|---|---|
| Oxidized nicotinamide coenzyme (Wako Junyaku Co., Ltd.) | 10.2 mg |
| Ascorbate oxidase (Toyo Jozo Co., Ltd.) | 45 u |
| Emulgen 935 (Kao Soap Co., Ltd.) | 0.4 g |
| Oxamic Acid (Aldrich Chemical Company, Inc.) | 45.6 mg |

The above components are dissolved in 10 ml of 0.4M Tris-HCl buffer, pH 7.8.

Three kinds of blood samples were tested according to the procedure detailed above to determine the amount of polyamines contained in each sample. The result is shown in Table 6.

TABLE 5

| | Sample | Sample | Standard | Standard | Test Blank | Test Blank |
|---|---|---|---|---|---|---|
| Standard (30 uM putrescine.2HCl soln.) | — | — | 0.5 ml | 0.5 ml | — | — |
| Sample | 0.5 ml | 0.5 ml | — | — | — | — |
| Test blank (pure water) | — | — | — | — | 0.5 ml | 0.5 ml |
| Reagent 1' | 0.5 ml | — | 0.5 ml | — | 0.5 ml | — |
| Reagent 3 | — | 0.5 ml | — | 0.5 ml | — | 0.5 ml |
| | Reaction at 37° C. for 20 minutes | | | | | |
| Reagent 2 | 0.5 ml | 0.5 ml | 0.5 ml | 0.5 ml | 0.5 ml | 0.5 ml |
| | Reaction at 37° C. for 5 minutes | | | | | |
| 1M Hydrochloric acid | 0.5 ml | 0.5 ml | 0.5 ml | 0.5 ml | 0.5 ml | 0.5 ml |
| | Measurement of absorbance at 530 nm | | | | | |
| Absorbance | $E_s$ | $E_s'$ | $E_{st}$ | $E_{st}'$ | $E_{H_2O}$ | $E_{H_2O}'$ |

The same blood samples as above were tested by high-performance liquid chromatography (HPLC) to determine the amount of polyamines. The result is also shown in Table 6.

TABLE 6

|  | Values obtained by the method of this invention | Values obtained by HPLC |
|---|---|---|
| Blood 1 | 9.6 | 10.0 |
| Blood 2 | 13.6 | 13.4 |
| Blood 3 | 4.6 | 5.0 |
|  |  | (Unit: umole/l) |

It is apparent from the table that the amount of polyamines in the blood can be accurately determined by the method of this invention.

EXAMPLE 2

Quantitative Determination Of Polyamines In Urine

The amount of polyamines in urine samples were determined in much the same manner as in Example 1 except that 0.5 ml of urine samples were used in place of the test solutions prepared from blood samples and that Reagent 1 was employed in place of Reagent 1'.

Measurement was made on three kinds of urine samples (five times for each). Values $E_2-E_2'$ for each sample are shown in Table 7, which indicate the high reproducibility of the method of this invention. Values of $E_{st}-E_{st}'$ and $^EH_2O-^EH_2O'$ were 0.146 and 0.013, respectively. The amount of polyamines in each sample was calculated from the value of $E_s-E_s'$ obtained in the first run of five tests. The results are also shown in Table 7.

Separately, the amounts of polyamines in these urine samples were measured by HPLC according to the procedure described below. To each of 1 ml of the urine samples, was added 1 ml of 0.1M phosphate buffer, pH 7.2, containing 240 units acylopolyamine amidohydrolase, and the mixture was heated at 37° C. for one hour to convert all the acylpolyamines involved to free polyamines. The precipitate was removed by centrifugation, 3 ml of the supernatant was passed through a minicolumn packed with a weakly acidic cation-exchange resin, the column was washed with pure water, and the adsorbed polyamines were eluted with 1 ml of 0.4M trichloroacetic acid solution. The eluate thus obtained was subjected to high-performance liquid chromatography (HPLC) to determine the amount of polyamines. The result is also shown in Table 7.

It is apparent from the table that the amount of polyamines contained in the urine can be accurately determined by the method of this invention.

TABLE 7

|  | Test No. | Urine 1 | Urine 2 | Urine 3 |
|---|---|---|---|---|
| Values of $E_s-E_s'$ | 1 | 0.146 | 0.234 | 0.547 |
|  | 2 | 0.145 | 0.233 | 0.545 |
|  | 3 | 0.145 | 0.232 | 0.543 |
|  | 4 | 0.146 | 0.234 | 0.548 |
|  | 5 | 0.147 | 0.233 | 0.546 |
|  | Average | 0.146 | 0.233 | 0.546 |
|  | Standard deviation | $8.37 \times 10^{-4}$ | $8.37 \times 10^{-4}$ | $1.92 \times 10^{-3}$ |
|  | C.V. | 0.57% | 0.36% | 0.35% |
| Amt. of polyamines (umole/l) |  | 30.0 | 49.8 | 120.5 |
| Amt. of polyamines by |  | 30.0 | 48.6 | 121.0 |

TABLE 7-continued

| Test No. | Urine 1 | Urine 2 | Urine 3 |
|---|---|---|---|
| HPLC (umole/l) | | | |

EXAMPLE 3

A urine sample containing 120 umole/1 polyamines (putrescine:cadaverine:spermidine = 1:1:1) was prepared. Separately was prepared a sample solution comprising the same urine as above but which contains pure water in place of the polyamines. The amount of polyamines in the urine sample was determined according to the procedure given below using the reagents of the following compositions.

(a) Reagents

| (Reagent 4) | |
|---|---|
| Ascorbate oxidase | 45 u |
| (Toyo Jozo Co., Ltd.) | |
| Putrescine oxidase | 80 u |
| (derived from *Micrococcus*) | |
| ω-Aminoalkylaldehyde dehydrogenase | 10 u |
| (derived from *Micrococcus*) | |
| Oxidized nicotinamide coenzyme | 10.2 mg |
| (Wako Junyaku Co., Ltd.) | |
| Emulgen 935 | 0.4 g |
| (Kao Soap Co., Ltd.) | |
| The above components are dissolved in 10 ml of 0.2M Tris-HCl buffer (pH 8.0). | |
| (Reagent 5) | |
| Nitro Tetrazolium Blue (Nitro-TB) | 5.0 mg |
| (Dojin Chemical Research Laboratories) | |
| Diaphorase | 80 u |
| (Oriental Enzyme Co., Ltd.) | |
| The above components are dissolved in 0.6M MES buffer, pH 6.0 (Dojin Chemical Research Laboratories) to make up a total volume of 20 ml. | |

(Reagent 6)

1M hydrochloric acid (b) Testing procedure

The urine samples prepared above were treated according to the procedure shown in Table 8 as described below. To 0.5 ml of each of the sample solutions, was added 0.5 ml of Reagent 4, and the mixture was heated at 37° C. for 20 minutes. 0.5 ml of Reagent 5, a tetrazolium color developer, was then added, pH was adjusted to 6.0, and the reaction was continued at 37° C. for five minutes. After addition of 0.5 ml 1M hydrochloric acid, the absorbance at 530 nm was measured.

TABLE 8

|  | Test Sample | Blank Sample |
|---|---|---|
| Urine containing polyamines | 0.5 ml | — |
| Urine containing no polyamines | — | 0.5 ml |
| Reagent 4 | 0.5 ml | 0.5 ml |
|  | Reaction at 37° C. for 20 minutes | |
| Reagent 5 | 0.5 ml | 0.5 ml |
|  | Reaction at 37° C. for 5 minutes | |
| Reagent 6 | 0.5 ml | 0.5 ml |
| Absorbance (A530) | $E_s$ | $E_b$ |

In the procedure shown in the above table, the amount of Eulugen 935 in Reagent 4 was varied so that its concentrtion was 0.8%, 1.2%, 3.0% and 5.0% after the addition of Reagent 5.

The amount of reduced nicotinamide coenzyme in the urine was calculated form the absorbance data obtained above using the following equation:

Concn. of reduced nicotinamide coenzyme in the urine (umole/l)

$$= \frac{(E_s - E_b)}{(\text{Molecular extinction coefficient})/2} \times (\text{Dilution factor}) \times 10^6$$

$$= 2 \times \frac{(E_s - E_b)}{3.6 \times 10_4} \times 4 \times 10^6$$

wherein the dilution factor represents that of the urine sample in the final step of the analytical process, and the molecular extinction coefficient is the theoretical value for the formazan dye.

Measurement under the same conditions was repeated five times, and the result is summarized in Table 9. From the absorbance data obtained above, the molecular extinction coefficients of the formazan dye under the different conditions were calculated, and also shown in Table 9.

It is apparent from Table 9 that the amount of polyamines can be determined very accurately and precisely by the method of this invention at a high sensitivity because of the sufficiently high values of molecular extinction coefficient.

TABLE 9

| Emulgen concn. (%) | | 0.8 | 1.2 | 3.0 | 5.0 |
|---|---|---|---|---|---|
| Poly- | 1 | 118.6 | 121.3 | 120.5 | 121.9 |
| amine | 2 | 119.0 | 120.1 | 121.3 | 120.8 |
| concen. | 3 | 119.1 | 118.2 | 122.0 | 121.6 |
| (umole/l) | 4 | 118.2 | 119.1 | 121.4 | 120.6 |
| | 5 | 118.0 | 122.5 | 120.6 | 121.0 |
| Average | | 118.6 | 120.2 | 121.2 | 121.1 |
| Standard deviation | | 0.482 | 1.71 | 0.629 | 0.497 |
| Coefficient of variation (%) | | 0.41 | 1.42 | 0.51 | 0.41 |
| Molecular extinction coefficient $(M^{-1} cm^{-1})$ | | $3.60 \times 10^4$ | $3.65 \times 10^4$ | $3.67 \times 10^4$ | $3.67 \times 10^4$ |

EXAMPLE 4

This examples examines the possible effects of the presence of reducing substances in the quantitive determination of polyamines by the method of this invention using the reagents with the folooing compositions. The result is summarized in Table 11.

(a) Reagents

| (Reagent 7) | |
|---|---|
| Putrescine oxidase | 80 u |
| (derived from *Micrococcus*) | |
| ω-Aminoalkylaldehyde dehydrogenase | 10 u |

| -continued | |
|---|---|
| (derived from *Micrococcus*) | |
| Oxidized nicotinamide coenzyme | 10.2 mg |
| (Wako Junyaku Co., Ltd.) | |
| Ascorbate oxidase | 40 u |
| (Toyo Jozo Co. Ltd.) | |
| The above components are dissolved in 10 ml of 0.2M Tris-HCl buffer (pH 8.0). | |
| (Reagent 8) | |
| Nitro Tetrazolium Blue (Nitro-TB) | 1.5 mg |
| (Dojin Chemical Research Laboratories) | |
| Diaphorase | 40 u |
| (Oriental Enzyme Co., Ltd.) | |
| Emulgen 935 | 0.4 g |
| The above components are dissolved in 20 ml of 0.2M MES buffer | |

(b) Testing procedure

Solutions containing known concentrations of polyamines and a reducing substance were diluted with a solution containing polyamines of a definite concentration, giving serial dilutions of the same polyamine concentration and of varying reducing substance concentrations. Separately, similar serial dilutions were prepared in which pure water was used in place of the polyamines. The test solutions were analyzed for the amount of polyamines contained using Hitachi Automatic Analyzer, Model 7050, to examine the effect of the various reducing agents.

To 20 ul of each of the test solutions was added 100 ul of Reagent 7, and the mixture was heated at 37° C. for five minutes, 250 ul of Reagent 8 was then added, and reaction was continued at 37° C. for five minutes at pH 6.0 and at a surfactant concentration of 1.35% to determine the amount of polyamines. A preliminary test showed that the absorbance of physiological saline containing 50 umole/l polyamines (standard solution) is 0.0475 (physiological saline used as the blank). Based on this value, conversion from absorbance data to polyamine concentration was made according to the following equations:

$$C1 = \frac{A1}{0.0475} \times 50$$

$$C2 = \frac{A2}{0.0475} \times 50$$

wherein A1 is the absorbance for the sample containing polyamines and A2 is the absorbance increase over blanks for the sample containing no polyamines.

The results obtained are summarized in Table 11.

It is apparent form Table 11 that, although a slight increase in the blanks was observed with ascorbic acid, no effect was noticed with the other reducing substances. With respect to the polyamine analytical values (C1–C2), none of the reducing substances had any effect at all. The color of formazan dye was also very stable, with no contamination of the cells used in the automatic analyzer nor precipitation of dye being observed.

TABLE 11

| Ascorbic acid | | | | Bilirubin | | | |
|---|---|---|---|---|---|---|---|
| Acorbic acid concn. (mg/dl) | C1 (uM) | C2 (uM) | C1–C2 (uM) | Bilirubin concn. (mg/dl) | C1 (uM) | C2 (uM) | C1–C2 (uM) |
| 0 | 84 | 0 | 84 | 0 | 84 | 0 | 84 |
| 25 | 86 | 1 | 85 | 0.25 | 83 | 0 | 83 |
| 50 | 86 | 1 | 85 | 0.50 | 84 | 0 | 84 |
| 75 | 87 | 2 | 85 | 0.75 | 84 | 0 | 84 |
| 100 | 88 | 3 | 85 | 1.00 | 84 | 0 | 84 |
| Reduced glutathione | | | | Uric acid | | | |

TABLE 11-continued

| Reduced glutathione concn. (mg/dl) | C1 (uM) | C2 (uM) | C1-C2 (uM) | Uric acid concn. (mg/dl) | C1 (uM) | C2 (uM) | C1-C2 (uM) |
| --- | --- | --- | --- | --- | --- | --- | --- |
| 0 | 86 | 0 | 86 | 0 | 84 | 0 | 84 |
| 25 | 88 | 0 | 88 | 0.25 | 85 | 0 | 84 |
| 50 | 87 | 0 | 87 | 0.50 | 85 | 0 | 85 |
| 75 | 86 | 0 | 86 | 0.75 | 84 | 0 | 84 |
| 100 | 88 | 0 | 85 | 1.00 | 84 | 0 | 84 |

EXAMPLE 5

The amounts of polyamines were determined according to the procedure given below, using the reagents with the following compositions to examine the effect of pH upon the determination of the reduced form of nicotinamide coenzyme. The result is shown in Table 12.

(a) Reagents (Reagent 9) that Emulgen 935 was used in an amount of 0.4 gram.

(Reagent 10)

Reagent similar to Reagent 5 described in Example 3 except that 0.6MMES buffer, pH 6.0, was replaced by buffers of various pH levels as shown in Table 12.

(Reagent 11)

1M hydrochloric acid (b) Testing procedure

Urine samples of the same compositions as those in Example 3 containing 60.0 umole/l polyamines were prepared. Separately, solutions comprising the same urine as above which contain pure water in place of polyamines were also prepared. The above urine samples were treated according to the procedure as described below. To each of the sample solutions, 0.5 ml, was added 0.5 ml of Reagent 9, and the mixture was heated at 37° C. for 20 minutes at pH 8.0. 0.5 ml of Reagent 10 was then added. The tetrazolium color developer was allowed to act at 37° C. for five minutes at different pH levels, 0.5 ml of Reagent 11 was added, and the absorbance at 530 nm was measured for 30 umole/l polyamine solution and for pure water (0.1465 and 0.013, respectively).

The measured amounts of polyamines shown in Table 12 were calculated from the absorbance data of sample solutions ($E_s$) and those for blank solutions ($E_b$) using the following equation:

$$\text{Concentration of polyamines (umole/l)} = 30 \times \frac{(E_s - E_b)}{0.146 - 0.013}$$

In Table 12 are also shown the average and the coefficient of variation (C.V.) of five measurements at each pH level.

TABLE 12

| PH | Polyamine Concentration (uM) | |
| --- | --- | --- |
|  | Average | C.V. (%) |
| 6.9 | 59.8 | 0.61 |
| 6.7 | 59.9 | 0.43 |
| 6.5 | 60.2 | 0.45 |
| 6.2 | 60.1 | 0.32 |
| 6.0 | 59.9 | 0.47 |
| 5.5 | 59.8 | 0.49 |
| 5.0 | 59.5 | 0.58 |
| 4.0 | 59.4 | 0.68 |

What is claimed is:

1. A method for the quantitative determination of polyamines, comprising:
   A. allowing a polyamine oxidizing enzyme, an ω-aminoalkylaldehyde dehydrogenase and an oxidized nicotinamide coenzyme to act upon a sample of body fluid containing polyamines, and
   B. measuring the reduced nicotinamide coenzyme thus formed, thereby determining the amount of the polyamines.

2. A method for quantitative determination of polyamines according to claim 1, wherein the polyamine oxidizing enzyme, ω-aminoalkylaldehyde dehydrogenase and oxidized nicotinamide coenzyme have been previously mixed to form a reagent, and the analysis is carried out by admixing the reagent to a sample of body fluid containing polyamines.

3. A method for quantitative determination of polyamines according to claim 1, wherein said polyamine oxidizing enzyme is first allowed to act upon a sample of body fluid containing polyamines, followed by addition of said ω-aminoalkylaldehyde dehydrogenase and oxidized nicotinamide coenzyme simultaneously or separately.

4. A method for the quantitative determination of polyamines according to claim 1, wherein said oxidized nicotinamide coenzyme is oxidized nicotinamide adenine dinucleotide or oxidized nicotinamide adenine dinucleotide phosphate.

5. A method for the quantitative determination of polyamines according to claims 1 wherein said ω-aminoalkylaldehyde dehydrogenase is 4-aminobutanal dehydrogenase.

6. A method for the quantitative determination of polyamines according to claim 2, wherein said ω-aminoalkylaldehyde dehydrogenase is 4-aminobutanal dehydrogenase.

7. A method for the quantitative determination of polyamines according to claim 3, wherein said ω-aminoalkylaldehyde dehydrogenase is 4-aminobutanal dehydrogenase.

8. A method for the quantitative determination of polyamines according to claim 4, wherein said ω-aminoalkylaldehyde dehydrogenase is 4-aminobutanal dehydrogenase.

9. A method for the quantitative determination of polyamines according to claim 1 wherein the amount of reduced nicotinamide coenzyme is determined by allowing a tetrazolium color developer and an electron carrier to act upon the solution containing said reduced-form coenzyme at a pH level in the range from 4 to 7 in the presence of a nonionic surfactant in an amount of 0.3 to 10 weight %, and measuring the intensity of color thus developed.

10. A method for the quantitative determination of polyamines according to claim 2 wherein the amount of reduced nicotinamide coenzyme is determined by allowing a tetrazolium color developer and an electron carrier to act upon the solution containing said reduced-form coenzyme at a pH level in the range from 4 to 7 in the presence of a nonionic surfactant in an amount of 0.3 to 10 weight %, and measuring the intensity of color thus developed.

11. A method for the quantitative determination of polyamines according to claim 3 wherein the amount of reduced nicotinamide coenzyme is determined by allowing a tetrazolium color developer and an electron carrier to act upon the solution containing said reduced-form coenzyme at a pH level in the range from 4 to 7 in the presence of a nonionic surfactant in an amount of 0.3 to 10 weight %, and measuring the intensity of color thus developed.

12. A method for the quantitative determination of polyamines according to claim 1 wherein an acylpolyamine amidohydrolase, a polyamine oxidizing enzyme, an ω-aminoalkylaldehyde dehydrogenase and an oxidized nicotinamide coenzyme are allowed to act upon the sample of urine, and the resulting reduction in nicotinamide coenzyme is measured so as to determine the amount of polyamines contained in the urine sample.

13. A method for the quantitative determination of polyam according to claim 1 wherein the polyamine oxidizing enzyme is a putrescine oxidase of microbial origin derived from strains of the genera Micrococcus, Nocardia, Aspergillus Pseudomonas or Arthrobacter.

14. A method for the quantitative determination of polyamines according to claim 2 wherein the polyamine oxidizing enzyme is a putrescine oxidase of microbial origin derived from strains of the genera Micrococcus, Nocardia, Aspergillus Pseudomonas or Arthrobacter.

15. A method for the quantitative determination of polyamines according to claim 3 wherein the polyamine oxidizing enzyme is a putrescine oxidase of microbial origin derived from strains of the genera Micrococcus, Nocardia, Aspergillus Pseudomonas or Arthrobacter.

16. A method for the quantitative determination of polyamines according to claim 4 wherein the polyamine oxidizing enzyme is a putrescine oxidase of microbial origin derived from strains of the genera Micrococcus, Nocardia, Aspergillus Pseudomonas or Arthrobacter.

17. A method for the quantitative determination of enzymes according to claim 1 wherein the polyamine oxidizing is a putrescine oxidase of plant origin derived from germinated soybean or a putrescine oxidase of animal origin derived from pig kidney.

18. A method for the quantitative determination of polyamines according to claim 2 wherein the polyamine oxidizing enzyme is a putrescine oxidase of plant origin derived from germinated soybean or a putrescine oxidase of animal origin derived from pig kidney.

19. A method for the quantitative determination of polyamines according to claim 3 wherein the polyamine oxidizing enzyme is a putrescine oxidase of plant origin derived from germinated soybean or a putrescine oxidase of animal origin derived from pig kidney.

20. A method for the quantitative determination of polyamines according to claim 4 wherein the polyamine oxidizing enzyme is a putrescine oxidase of plant origin derived from germinated soybean or a putrescine oxidase of animal origin derived from pig kidney.

21. 4-Aminobutanan dehydrogenase having the following properties:

(1) reactive with 4-aminobutanal in the presence of oxidized nicotinamide adenine dinucleotide or oxidized nicotinamide adenine dinucleotide phosphate to form 4-aminobutyric acid and reduced nicotinamide adenine dinucleotide or reduced nicotinamide adenine dinucleotide phosphate;

(2) coactive with oxidized nicotinamide adenine dinucleotide and oxidized nicotinamide adenine dinucleotide phosphate as an oxidized-form nicotinamide coenzyme, and upon 4-aminobutanal and 5-aminopentanal as ω-aminoalkyladehyde dehydrogenase;

(3) having an optimum pH in the range of about 7.7 to 8.3;

(4) retaining more than 90% activity at pH in the range from 4.5 to 8.5 when stored at 5° C. for 24 hours;

(5) having a molecular weight of 102,000±5,000;

(6) having two subunits where the molecular weights of the subunits are 50,000±5,000; and (7) having a specific activity of 120 to 140 units/mg protein.

22. A process for the production of 4-aminobutanal-dehydrogenase according to claim 22 which comprises cultivating cells of a strain of Micrococcus capable of producing said 4-aminobutanaldehydrogenase in a culture medium containing carbon sources, nitrogen sources and inorganic salts at a temperature in the range of 15° C. to 40° C. and at a pH in the range of from 4.0 to 9.0 and then isloating the 4-aminobutanal dehydrogenase produced from the grown cells.

23. A process as claimed in claim 22, wherein putrescine, spermidine, diaminopropane or cardin is added to said culture medium.

24. A colorimetric method for the quantitive determiniation of polyamines in a body fluid comprising:

A. reacting a sample body fluid with 0.1 t 50 units of polyamine oxidizing enzyme, 0.1 to 50 uinits of an ω-aminoalkylaldehyde dehydrogenase and oxidized nicotinamide coenzyme and converting any conjugated polyamines which may be present to free polyamines by using acylpolyamine amidohydrolase;

B. adding 0.01 to 50 mM of a dye selected from the group consisting of tetrazolium salts, and an electron carrier selected from the group consisting of diaphorase and 1-methoxy-5-methyl phenazinium methyl sulfate in the presence of 0.3% to 10% by weight of a nonionic surfactant at a pH in the range of about 4 to 7; and C. measuring the absrobance at about 530 nm of the test solution as compared with a standard solution containing a known amount of a polyamine.

25. A method according to claim 24 wherein ω-aminoalkylaldehyde dehydrogenase is 4-aminobutanal dehydrogenase and the reaction of step A is conducted at a pH in the range of 6.5 to 8.5

26. A method according to claim 24 wherein the dye is Ntiro Tetraxolium Blue and the electron carrier is diaphorase.

27. A method according to claim 25 wherein the dye is Nitro Tetraxolium Blue and the electron carrier is a diaphorase.

* * * * *